(12) United States Patent  
Matijczyk

(10) Patent No.: US 7,180,587 B1
(45) Date of Patent: Feb. 20, 2007

(54) GUN BARREL INSPECTION MIRROR DEVICE

(76) Inventor: Max A. Matijczyk, 316 N. Main St., Webberville, MI (US) 48892

( * ) Notice: Subject to any disclaimer, the term of this patent is extended or adjusted under 35 U.S.C. 154(b) by 367 days.

(21) Appl. No.: 10/792,970

(22) Filed: Mar. 4, 2004

Related U.S. Application Data

(60) Provisional application No. 60/452,031, filed on Mar. 4, 2003.

(51) Int. Cl.
G01N 21/00 (2006.01)

(52) U.S. Cl. .................................... 356/241.2
(58) Field of Classification Search ... 356/241.1–241.6
See application file for complete search history.

(56) References Cited

U.S. PATENT DOCUMENTS

| 399,286 A | * | 3/1889 | Russell ..................... 356/241.2 |
| 1,329,366 A | | 2/1920 | Careaga et al. |
| 1,775,452 A | | 9/1930 | Fisher |
| 2,793,561 A | | 5/1957 | Jacobus |
| 2,794,363 A | | 6/1957 | Parfitt |
| 3,228,108 A | * | 1/1966 | Chaperon ................ 356/241.2 |
| 3,423,154 A | | 1/1969 | Weber, Jr. |
| 5,365,332 A | | 11/1994 | Barber, Jr. et al. |
| D357,490 S | | 4/1995 | Browning |
| D369,365 S | | 4/1996 | Waring |

* cited by examiner

Primary Examiner—Gregory J. Toatley, Jr.
Assistant Examiner—Patrick J Connolly
(74) Attorney, Agent, or Firm—Cargill & Associates, P.L.L.C.

(57) ABSTRACT

This inspection device includes an open ended, elongated sighting tube with an optical inspection window in the outer circumference for binocular viewing of the chamber. The elongated sighting tube is generally cylindrical and has a relatively short dimension of between about 1" and 2" and the sighting tube has a longitudinal axis which coincides with the longitudinal centerline of the gun barrel when the gun barrel inspection device is placed into position in the breech. A substantially circular angled specular flat plate mirror of a relatively thin dimension of from about 1⁄32" to about 3⁄32" is attached with the tube to an angled back plate plug that terminates in a substantially circular angled flat surface to receive and support the angled mirror. The back plate plug is sized to be inserted into the open end of the elongated sighting tube to position the angled mirror in a supported arrangement within full view in the optical inspection window. The optical inspection window allows for full binocular vision down the barrel of the gun and the mirror reflects the entire barrel of the gun.

4 Claims, 1 Drawing Sheet

GUN BARREL INSPECTION MIRROR DEVICE

CROSS REFERENCES TO RELATED APPLICATIONS

This application claims the benefit of U.S. Provisional Application No. 60/452,031 filed on Mar. 4, 2003.

BACKGROUND OF THE INVENTION

1. Field of the Invention

The present invention relates to gun barrel inspection devices, and it is more particularly directed to a gun bore scope used for inspecting gun bores of any caliber, and allowing for the use of binocular vision, rather than having to use only one eye.

2. Description of the Prior Art

Obstructions in gun barrels have caused many accidents and deaths over the coarse of the past several hundred years, and it is incumbent upon the gun user to make sure that there is no blockage in the barrel prior to igniting the firearm. Many deaths and injuries have occurred during the procedure of cleaning a gun, because the person cleaning the gun did not know that there was a bullet in the barrel of the gun before he proceeded with the cleaning.

As anyone who uses a gun knows, it is very uncomfortable to look down the bore of the gun in order to determine if there is any blockage. No one wants to look with his eye directly down the barrel in order to make such a determination for fear of the gun going off. Simple devices have been attempted in the past in order to make inspections on particular firearms during the cleaning process to look for blockages, obstructions, bullets, and also to do inspections for wear of the rifle or gun barrel itself.

There are certain problems which have been inherent in all of the prior art devices, including the fact that they are generally rifle specific, and they would not fit in a bolt action, autoloader, or lever action firearm. Another problem present in the prior art devices include the fact that the mirror did not reflect the entire barrel of the firearm, but merely a small portion of the firearm due to the configuration of the bore scope/inspection device. Yet another problem with the prior art devices was that the bore scope was of a fragile nature and could not easily be put into one's pocket or gun pouch without the fear of small parts breaking off. A sturdy gun bore scope/inspection device is much needed, especially one that will fit into all gun bores, regardless of caliber, or of type, in order for a marksman or hunter to utilize the bore scope on a regular basis.

Furthermore, defects in the gun barrel can be reviewed, but the relevant prior art devices have required that the gun user close one eye in order to look through the inspection device in order to look for obstructions.

In order to provide a proper inspection, including the full use of a typical human's depth perception by the use of both of their eyes, it is important that an inspection device be of such a configuration that a person can utilize both of their eyes, i.e. binocular vision, in order to determine the location of the obstruction and/or the defect.

Furthermore, it would be an advantage for the present invention to provide such a gun bore scope with structural integrity such that the piece may be put in the pocket or gun case of the gun user. This allows the gun user to check the gun in the field for any need to clean or unblock the barrel itself.

In a previous attempt to provide such a gun bore scope, U.S. Pat. No. 2,794,363 issued to Parfitt on Jun. 4, 1957, discloses a gun mirror inspection device for use in conjunction with firearms and for inspecting their respective barrels. These gun scope were issued by the U.S. military, but were soon discarded because the configuration of the device itself and the angle of the mirror only allows a small portion of the barrel to be inspected. Furthermore, the inspection device requires that the user close one eye and look through the mirror with only one eye, which removes the ability to use his binocular vision.

U.S. Patent No. Des. 357,490 issued to Browning on Apr. 18, 1995, discloses a design for a scope for a specific rifle bore. This device includes a mirrored surface, although the mirrored surface once again is located in such a configuration that only a small portion of the rifle bore can be inspected. Looking especially to FIG. 4, it can be seen that only approximately the top 1/8 of the barrel can be seen when looking at the optics of the location of the mirror.

Therefore, it is an object of the present invention to provide a gun bore inspection scope that is small, lightweight, compact and capable of being put into one's pocket without being destroyed.

It is yet a further object of the present invention to provide a gun bore scope inspection device that can be used with both eyes, in order to enable the full use of the human depth perception which comes from using both eyes to view something.

SUMMARY OF THE INVENTION

In accordance with the above-noted advantages and desires of the industry, the present invention provides a gun barrel inspection device for inspecting a firearm chamber through the breech. This inspection device includes an open ended, elongated sighting tube with an optical inspection window in the outer circumference for binocular viewing of the chamber. The elongated sighting tube is generally cylindrical and has a relatively short dimension of between about 1" and 2" and the sighting tube has a longitudinal axis which coincides with the longitudinal centerline of the gun barrel when the gun barrel inspection device is placed into position in the breech.

A substantially circular angled specular flat plate mirror of a relatively thin dimension of from about 1/32" to about 3/32" is attached with the tube to an angled back plate plug that terminates in a substantially circular angled flat surface to receive and support the angled mirror. The back plate plug is sized to be inserted into the open end of the elongated sighting tube to position the angled mirror in a supported arrangement within full view in the optical inspection window. The optical inspection window allows for full binocular vision down the barrel of the gun and the mirror reflects the entire barrel of the gun.

Although the invention will be described by way of examples hereinbelow for specific embodiments having certain features, it must also be realized that minor modifications that do not require undo experimentation on the part of the practitioner are covered within the scope and breadth of this invention. Additional advantages and other novel features of the present invention will be set forth in the description that follows and in particular will be apparent to those skilled in the art upon examination or may be learned within the practice of the invention. Therefore, the invention is capable of many other different embodiments and its details are capable of modifications of various aspects which will be obvious to those of ordinary skill in the art all without departing from the spirit of the present invention. Accordingly, the rest of the description will be regarded as illustrative rather than restrictive.

BRIEF DESCRIPTION OF THE DRAWINGS

These and other objects of the invention will become apparent to those skilled in the art, when taken in conjunction with the following detailed description of the invention and in combination with the accompanying drawings, in which.

DETAILED DESCRIPTION OF THE INVENTION

Figure 1:
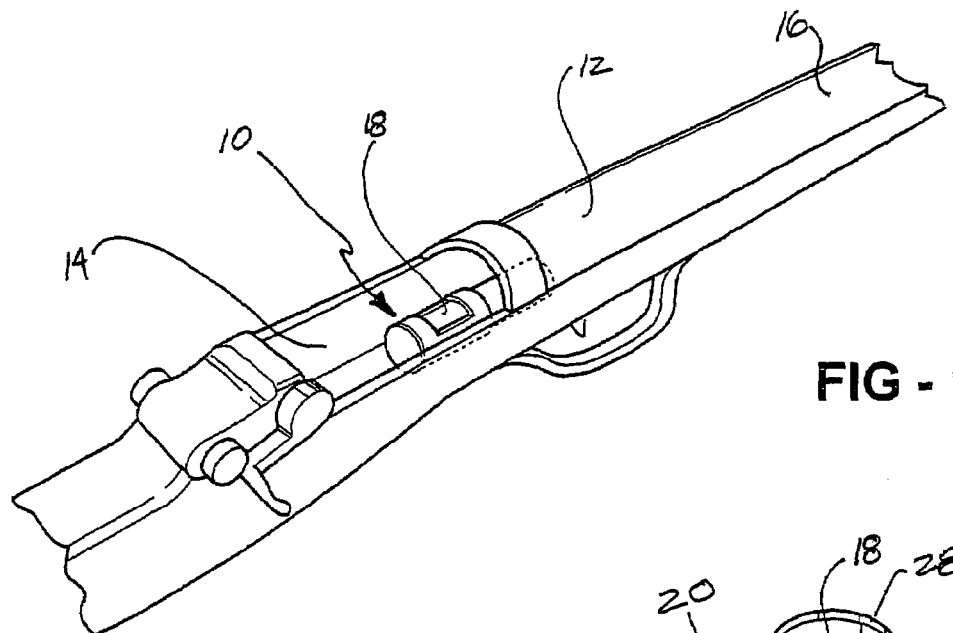
FIG. 1 is a perspective view of the gun bore scope of the present invention in the breech of a rifle, located so that the gun bore scope can inspect the bore of the rifle.

In accordance with the present invention, and in order to achieve the above-mentioned objects and advantages, the present invention discloses a gun bore scope inspecting device which utilizes a mirror in order to allow a gun user to inspect the gun or rifle barrel. Like elements and characters will follow through from FIGS. 1 thru 3, wherein the gun bore scope itself is generally denoted by the numeral 10 representing the new gun bore scope. In FIG. 1, there is shown a gun bore inspection device in the breech of a rifle, illustrating its relative placement during use. The present invention will fit into any center fire rifle firearm.

FIG. 1 illustrates the gun bore scope 10 located in gun 12 within the breech 14 of the rifle. The inspection window 18 of gun bore scope 10 is directed down barrel 16 of a rifle. As can be seen in FIG. 1, the inspection window 18 is facing up so that the gun user can simply use both eyes to look down into the inspection device at the mirror and can inspect the entire length of the rifle barrel if only a small bit of light is coming down the rifle barrel 16. Further, as can be seen from FIG. 1, there is no necessity for the gun user to risk injury to look back up through the barrel into the breech from the end of the gun barrel in order to see any bullets or other obstructions.

Figure 2:
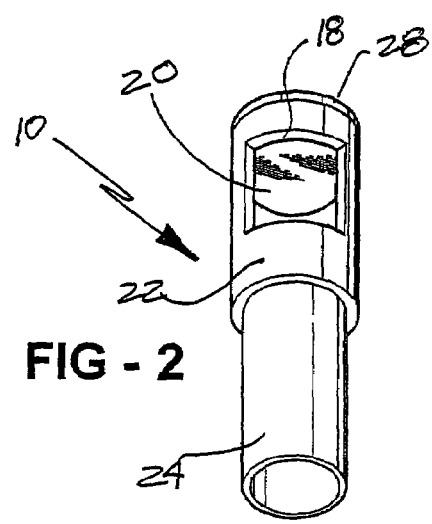
FIG. 2 is a plan view of the gun bore scope inspecting device of the present invention illustrating the relative placement of the mirror.

Looking next to FIG. 2, gun bore scope 10 is shown with a flat plate mirror 20 in its relative position. Mirror 20 is a relatively thin flat plate mirror in a substantially circular configuration, from about 1/32" to 3/32" thick, and about one-half (1/2) inch in diameter. It can be seen that the entire barrel may be inspected through inspection window 18. The placement of the mirror means that the entire bore can be seen in the mirror. There is a mirror collar 22 which surrounds the area holding the mirror. Mirror collar 22 is integral with the inspection scope barrel 24. Inspection scope barrel 24 helps to align the gun scope within the barrel of the gun once it has been inserted through the breech to get a good view up the barrel.

Figure 3:
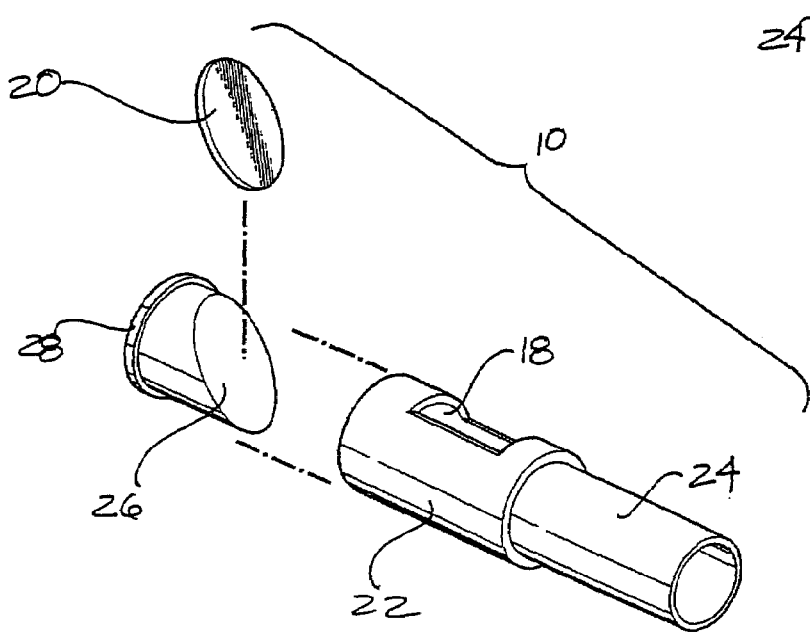
FIG. 3 is a side perspective exploded view of the gun bore scope of the present invention to illustrate the various components and their relative location.

Looking last to FIG. 3, there is shown an exploded view of the gun bore scope 10 with the relative placement of mirror 20 secured to a mirror back plate plug substrate 26 integral with a substrate lip 28. Mirror 20 is preferably permanently secured or glued to the substrate 26, and then the entire substrate assembly, including substrate lip 28, is inserted into the mirror collar 22. Aligning mirror 20 into a position so that when a user looks through inspection window 18 the entire barrel can be viewed through mirror 20. Substrate lip 28 abuts up against the end of mirror collar 22, and the substrate unit may be glued or otherwise secured into place within mirror collar 22. In the present embodiment, inspection scope barrel 24 is integral with the mirror collar 22, although they may be separate pieces glued together. The mirror substrate 26 is preferably machined from a single piece of metal, for example, aluminum, and has an outer diameter which will nest within the mirror collar inner diameter, still allowing for space for permanent securement or gluing. The substrate lip 28 butts up against the end of mirror collar 22, preventing mirror 20 from extending too far into the mirror collar, thereby obstructing vision of the full gun barrel 16.

In the preferred embodiment of the present invention, the entire gun bore scope is machined from aluminum, and is a single piece, save the plate plug 26, which obviously has to be a separate piece. Because the piece is preferably integral with itself, the gun bore scope can be thrown into a gun user's pocket, with a low likelihood of breaking it. However, it is envisioned by the present inventor that each of the components may be separately made out of any suitable material, including wood, plastic, metal, fiberglass, paper, cardboard, or the like, and the individual components may be secured together after the pieces are put into place.

Although the mirror face is preferably round so that a full inspection can be done of the inside barrel, it is also foreseen by the present inventor that the mirror face can be of a square, oval or rectangular configuration for inspecting other portions of a gun. Also, although a mirror is the preferred reflective surface for the present invention, it must be understood that other reflecting elements can be utilized and similarly situated within the gun bore scope. This means that highly polished steel, or other metal may be utilized, in order to totally eliminate breakage of the mirror in the pocket of the wearer. However, it must be noted that mirror 20 is of such a small size, and is so well protected within the gun bore scope of the present invention, that it is highly unlikely that the mirror would shatter during normal use or transport.

The reflecting surface of mirror 20 is preferably situated at an approximately 45-degree angle on the mirror back substrate 26 with relation to the longitudinal axis of the scope. It is envisioned by the present inventor that slight variations on that mounting angle may be usable, depending upon the inspection being preformed, although a fundamental inspection of the gun barrel is preferred at a 45 degree angle. The gun bore scope user can utilize both eyes to look down through the inspection window and see the full and round gun barrel in order to give a full visual observation and inspection to determine the presence of bullets, or to look for lead fouling, pits, barrel degradations, or any foreign objects or instructions in the barrel which would act as a detriment to perfect operation of the gun.

Although not illustrated, the present invention may also include a handle of any sort to help retrieve the scope from the breech. In order to perform an inspection, the action of the gun must be opened up to reveal the breech of the gun. The gun bore scope is inserted into the breech with the mirror facing the gun barrel, so that the inspection window is easily seen by the user from above the breech of the gun. Any gun cleaning implements, such as rods, cotton, patches, oils and the like may be inserted into the barrel after the inspection has taken place. Such implements are commonly used to remove dirt, lead fouling, and any other foreign objects through the bore of the gun. Gun cleaning conventionally used these implements first, and then the gun inspections were performed. However, it is the object of the present invention to provide a visual inspection prior to cleaning the gun, so that the person cleaning the gun will know whether or not there are any dangerous materials in the barrel of the gun prior to them sticking the gun cleaning implements therein.

Due to the round design of the present invention, gun bore scope 10 may be utilized with various calibers of firearms, and will work equally well in both large and small caliber. The reflection of light rays of mirror 20 may come from any light source through the gun barrel itself, such that a clear, non-obstructed inspection of the length of the bore of the rifle may be performed by an observer. The intensity of the light through the end of the gun barrel 16 is naturally restricted as a result of the light rays being introduced through the gun barrel, in the darkness of barrel. It has been determined by the present inventor that sufficient light coming through the barrel of the gun will provide an image in the mirror that the observer can utilize. This technique and gun bore scope may be utilized on larger caliber weapons, including shotguns and rifles, in the same manner which is described hereinabove with reference to the gun bore scope 10. Simple manipulations of the gun bore scope by the observer can be used in order to give a full inspection of any larger caliber firearm.

Therefore, in accordance with the objects and advantages first described hereinabove, we believe that our invention of a gun bore scope achieves all of those objects and advantages, and provides a gun bore scope which has superior utility and novelty over those described in the prior art. The basic principles of our invention have been explained in such a manner that it may be readily practiced by those skilled in the art without any undo experimentation. We have included what we consider to be the best embodiment of the invention, although we have described various other embodiments which may be utilized in carrying out and practicing the device and method of the present invention. It must be clearly understood that within the scope of the present invention, the invention may be practiced otherwise than as specifically described herein, by those who have ordinary skill in the art, in order to achieve the benefit of our invention.

The foregoing description of a preferred embodiment of the invention has been presented for purposes of illustration and description. It is not intended to be exhaustive or to limit the invention to the precise form disclosed. Obvious modifications or variations are possible in light of the above teachings with regards to the specific embodiments. The embodiment was chosen and described in order to best illustrate the principles of the invention and its practical applications to thereby enable one of ordinary skill in the art to best utilize the invention in various embodiments and with various modifications as are suited to the particular use contemplated. It is intended that the scope of the invention be defined by the claims which are appended hereto.

What is claimed is:

1. A gun barrel inspection device for inspecting a firearm chamber through the breech, comprising:

an open ended, elongated sighting tube with an optical inspection window in the outer circumference for binocular viewing of the chamber, said elongated sighting tube being generally cylindrical and having a relatively short dimension of between about 1" and 2", said sighting tube having a longitudinal axis which coincides with the longitudinal centerline of the gun barrel when the gun barrel inspection device is placed into position in the breech;

a substantially circular angled specular flat plate mirror of a relatively thin dimension of from about $\frac{1}{32}$" to about $\frac{3}{32}$"; and an angled back plate plug terminating in a substantially circular angled flat surface to receive and support the angled mirror, said back plate plug being sized to be inserted into the open end of the elongated sighting tube to position the angled mirror in a supported arrangement within full view in the optical inspection window, wherein the optical inspection window allows for full binocular vision down the barrel of the gun and the mirror reflects the entire barrel of the gun.

2. The inspection device of claim 1, wherein the mirror is round and about $\frac{1}{2}$" in diameter.

3. The inspection device of claim 1, wherein the optical inspection window is rectangular in dimension, and the window extends through the outer circumference of the sighting tube into the interior of the tube to an extent of from about 5° arc circumference to about 180° arc circumference, in order to provide a full view of the mirror held within, and to give stability to the inspection device so that it may be easily carried in a pocket or gun pouch without being damaged.

4. The inspection device of claim 1, wherein the sighting tube has an inner diameter dimension of about $\frac{1}{2}$" to receive the back plate plug securely therein while the mirror attached thereto is positioned and adapted to reveal the entire barrel of the gun.

\* \* \* \* \*